United States Patent [19]

Cooper et al.

[11] Patent Number: 5,238,926
[45] Date of Patent: Aug. 24, 1993

[54] ANTI-FUNGAL AGENTS

[75] Inventors: Alan B. Cooper, West Caldwell; Anil K. Saksena, Upper Montclair; Raymond Lovey, West Caldwell; Viyyoor Girijavallabhan, Parsippany; Ashit Ganguly, Upper Montclair, all of N.J.

[73] Assignee: Schering Corporation, Kenilworth, N.J.

[21] Appl. No.: 926,017

[22] Filed: Aug. 7, 1992

Related U.S. Application Data

[63] Continuation of Ser. No. 747,544, Aug. 20, 1991, abandoned.

[51] Int. Cl.$^5$ ............... A61K 31/70; A61K 31/41; C07H 17/00
[52] U.S. Cl. ........................ 514/50; 514/43; 514/49; 536/28.53; 536/28.54; 536/28.8; 536/28.7
[58] Field of Search ............ 536/23; 514/43, 49, 514/50

[56] References Cited

U.S. PATENT DOCUMENTS

| | | | |
|---|---|---|---|
| 4,158,608 | 6/1979 | Dähn et al. | 536/24 |
| 4,315,922 | 2/1982 | Hagenmaier et al. | 536/23 |
| 4,552,954 | 11/1985 | Moeschler et al. | 536/24 |
| 4,585,761 | 4/1986 | Zähner et al. | 514/43 |
| 4,914,087 | 4/1990 | Hector et al. | 514/50 |

FOREIGN PATENT DOCUMENTS 330923  9/1989  European Pat. Off.

OTHER PUBLICATIONS

CAS on line search computer print out.
Hass et al. CA 97-198538a (1982).
Shenbagamurthi et al. CA 104-183173s (1986).
Smith et al. CA 106-192579x (1987).
Decker et al. CA 113-129235m (1990).
*Antimicrobial Agents and Chemotherapy*, Apr., 1990, pp. 587-593.
*J. Org. Chem.*, 1986, 51, pp. 2307-2314, Boehm et al.
*Antimicrobial Agents and Chemotherapy*, Nov. 1983, pp. 787-796.
Shenbagamurthi *J. Med. Chem*, 1986, 29, pp. 802-809.
*J. Med Chem*, 1988, 31, pp. 650-656, Khare et al.
*J. Org. Chem.*, 1990, 55, pp. 3372-3787, Garner et al.
*Tetrahedron Letters*, vol. 30, 38, pp. 5065-5068 (1984) Garner et al; JACS, Jul. 28, 1971, pp. 3812-3813.
J. Org. Chem. 1986, 51, 2307-2314.
J. Med. Chem. 1986, 29, 802-809.
CA 106: 192579x with computer printout.
New Synthetic Polyoxin Analogs for Chitin Synthesis Inhibition, Smith et al., Chitin Nat. Technol. 3rd, 1985 pp. 197-202.

*Primary Examiner*—Cecilia Tsang
*Attorney, Agent, or Firm*—Eric S. Dicker; John J. Maitner; Matthew Boxer

[57] ABSTRACT

Compounds of the formula

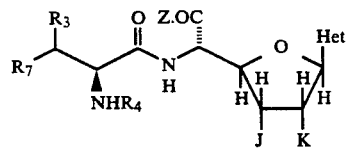

or pharmaceutically acceptable salts thereof
wherein $R_3$, $R_4$, $R_7$, J, K, Z and Het are as set forth herein are described.

The compounds of formula I are useful as agents in the treatment of fungal infections.

8 Claims, No Drawings

ANTI-FUNGAL AGENTS

This is a continuation of application Ser. No. 07/747,544 filed Aug. 20, 1991 now abandoned.

SUMMARY OF THE INVENTION

The invention relates to compounds of the formula

I or pharmaceutically acceptable salts thereof wherein:
Het is

R is H, COOH; $C_1-C_{12}$alkyl; CHO, CN; $CH_2OH$; or $CONH_2$;

$R_3$ is H, OH, $OCH_3$, $C_1-C_4$ alkyl, $CF_3$, or F $R_4$ is H, a natural amino acid attached by a peptide bond, or a metabolizable group;

$R_7$ is n is 1 to 16;
wherein Z is $R_5NR_6$, wherein Z' is $R_5NR_6$, $R_5$ is H, a saturated or unsaturated $C_6-C_{18}$ aliphatic side chain; or a hydroxylated $C_6-C_{18}$ aliphatic side chain;

$R_6$ is H; OH; O-benzyl; O-aryl; O-$(C_4-C_{14})$alkyl; alkyl $(C_1-C_{12})$; phenyl; substituted phenyl; or NHCO-$R_7$;

$R_8$ is $C_1-C_{16}$ alkyl; H, aryl or alkylaryl, with the proviso that $R_8$ cannot be H when when $R_7$ is J is H or OH;
K is H or OH.

Preferred are compounds of formula I wherein Het is uracil.

Also preferred are compounds of formula I wherein $R_4$ is H.

Most preferred are compounds of formula I wherein $R_5$ is $-(CH_2)_{11}CH_3$.

Also preferred are compounds where J and K are both OH.

As used herein, the UR denotes uracil. Uracil has the structure:

The term UPOC denotes uracil polyoxin C. The structural formula for UPOC is

Alkyl denotes straight or branched hydrocarbon chains, which contain from 1 to 20 carbon atoms. Representative examples include methyl, ethyl, propyl, decyl, dodecyl and the like. Alternatively, the number of carbon atoms in a particular alkyl may be specified. For example, $C_1-C_6$ alkyl refers to an alkyl which may have one to six carbon atoms.

Alkoxy denotes -O-alkyl wherein alkyl is as described above.

The term natural amino acid denotes the following amino acids; glycine and the following acids which have an L-configuration: valine, leucine, isoleucine, serine, aspartic acid, asparagine, glutamic acid, histidine, alanine, proline, phenylalanine, tryptophan, methionine, threonine, cysteine, tyrosine, glutamine, lysine and arginine which are also referred to respectively by the following abbreviations:

Gly, Val, Leu, Ile, Ser, Asp, Asn, Glu, His, Ala, Pro, Phe, Trp, Met, Thr, Cys, Tyr, Gln, Lys and Arg.

The term metabolizable group denotes any group which under metabolizable conditions (that is, when subjected to metabolic enzymes and the like) will be cleaved off. An example is

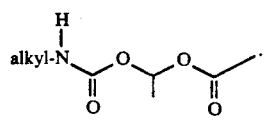

The term saturated aliphatic side chain denotes a saturated side chain containing only carbons and hydrogen. The saturated aliphatic side chain may contain up to 20 carbon atoms. Alternatively, the number of carbon atoms in an unsaturated aliphatic side chain may be specified. For example, a saturated $C_6$–$C_{18}$ aliphatic side chain denotes a saturated aliphatic side chain having from 6 to 18 carbon atoms. The saturated aliphatic side chain may contain within the chain up to three of any combination of the heteroatoms O, S, or N, with the proviso that such heteroatoms cannot be adjacent to each other in the chain.

The term unsaturated aliphatic side chain denotes an aliphatic side chain containing up to three double or triple bonds or any combination thereof. For example an unsaturated aliphatic side chain may contain three double bonds, two double bonds and one triple bond, one double bond and two triple bonds, or three triple bonds. The unsaturated aliphatic side chain may contain up to 20 carbon atoms. Alternatively, the number of carbon atoms in an unsaturated aliphatic side chain may be specified. For example, a unsaturated $C_6$–$C_{18}$ aliphatic side chain denotes an unsaturated aliphatic side chain having from 6 to 18 carbon atoms. The unsaturated aliphatic side chain may contain within the chain up to three of any combination of the heteroatoms O, S, or N, with the proviso that such heteroatoms cannot be adjacent to each other in the chain.

A hydroxylated aliphatic side chain denotes an aliphatic side chain as described above, wherein up to 3 hydrogens are replaced by OH. The hydroxylated aliphatic side chain may contain up to 20 carbon atoms. Alternatively, the number of carbon atoms in an hydroxylated aliphatic side chain may be specified. For example, a hydroxylated $C_6$–$C_{18}$ aliphatic side chain denotes an hydroxylated aliphatic side chain having from 6 to 18 carbon atoms. The hydroxylated aliphatic side chain may contain within the chain up to three of any combination of the heteroatoms O, S, or N, with the proviso that such heteroatoms cannot be adjacent to each other in the chain.

Aryl denotes a mono or bi-cyclic aromatic system. Examples of preferred aryl groups include those having from 6 to 14 carbon atoms. Representative examples include phenyl, 1-naphthyl, 2-naphthyl, and indanyl. The aryl group may contain additional substituents selected from the group consisting of: halogen atoms (e.g. Cl, Br, F and/or I), —O—alkyl, alkyl, and amino.

Alkylaryl denotes an aryl as described herein, wherein one of the hydrogens of the aryl is substituted by an alkyl as described herein.

A substituted phenyl refers to a phenyl bearing up to three substituents independently selected from the group consisting of —S—alkyl, —S—H, amino, $NO_2$, and —O—alkyl; and up to five substituents independently selected from the group consisting of fluoro, alkyl, and OH.

As used herein, a boldfaced bond, ▬ denotes a bond which comes up out of the plane of the page. A dashed bond, ⁓ denotes a bond which comes down below of the plane of the page. A curved bond, ⁓ denotes a racemic mixture.

Exemplary compounds of the invention include:

[Structure shown with $R_3$, $R_7$, NHR$_4$, Z.OC, O, UR, OH OH groups]

| No. | (structure with $R_3$, $R_7$, NHR$_4$, CO) | Z.OC |
|-----|--------------------------------------------|------|
| 1. | CH$_3$ with vinyl group, NH$_2$, CO | CONH(CH$_2$)$_{11}$CH$_3$ |
| 2. | CH$_3$–S(=O)–CH$_2$CH$_2$–, NH$_2$, CO | CONH(CH$_2$)$_{11}$CH$_3$ |
| 3. | (CH$_3$)$_2$–S–CH$_2$–, NH$_2$, CO | CONH(CH$_2$)$_{11}$CH$_3$ |
| 4. | H$_2$N–C(=O)–O–CH$_2$–CH(OH)–CH(OH)–, NH$_2$, CO | CONH(CH$_2$)$_{11}$CH$_3$ |
| 5. | CH$_3$–O–CH$_2$CH$_2$–, NH$_2$, CO | CONH(CH$_2$)$_{11}$CH$_3$ |
| 6. | PhCH$_2$–S–CH$_2$–, NH$_2$, CO | CONH(CH$_2$)$_{11}$CH$_3$ |
| 7. | CH$_3$(CH$_2$)$_9$–, NH$_2$, CO | CONH$_2$ |
| 8. | CH$_3$(CH$_2$)$_3$–, NH$_2$, CO | CONH(CH$_2$)$_{11}$CH$_3$ |

-continued

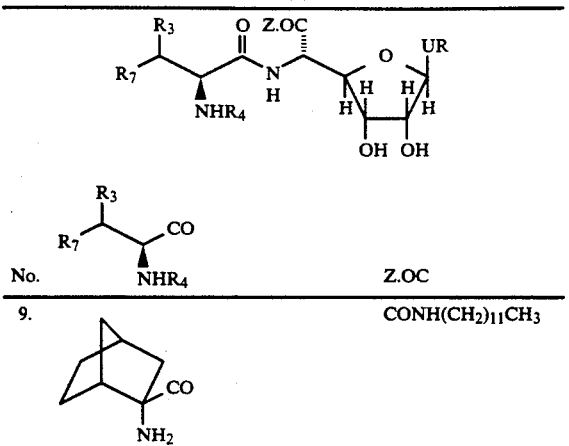

| No. | | |
|---|---|---|
| 9. | 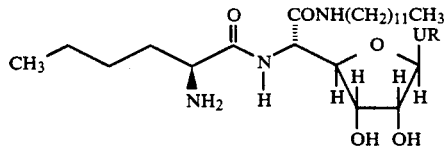 | CONH(CH$_2$)$_{11}$CH$_3$ |

Preferred compounds of the invention are:

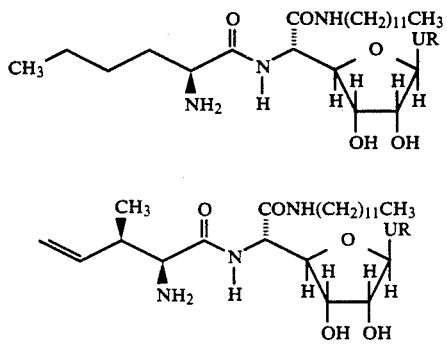

and or pharmaceutically acceptable salts thereof.

The most preferred compound of the invention is or a pharmacuutically acceptable salt thereof.

The invention also relates to pharmaceutical compositions which comprises a compound of formula I in combination with a pharmaceutically acceptable carrier material.

The invention also relates to a method for treating fungi which comprises administering to a mammal in need of such treatment an anti-fungally effective effective amount of a compound of formula I for such purpose.

DETAILED DESCRIPTION OF THE INVENTION

Asymmetric centers exist in compounds of formula I of the invention. Accordingly, compounds of formula I include stereoisomers.

All such isomeric forms and mixtures thereof are within the scope of the present invention. Unless otherwise indicated, the methods of preparation disclosed herein may result in product distributions which include all possible stereoisomers, although it is understood that physiological response may vary according to stereochemical structure. The isomers may be separated by conventional means such as fractional crystallization or HPLC (high performance liquid chromatography).

The compounds of formula I can exist in unsolvated as well as solvated forms, including hydrated forms, e.g. the hemihydrate. In general, the solvated forms, with pharmaceutically acceptable solvents such as water, ethanol, and the like are equivalent to the unsolvated forms for the purposes of the invention.

The compounds of formula I form pharmaceutically acceptable salts. The preferred pharmaceutically acceptable salts are nontoxic acid addition salts formed by adding to a compound of the invention about a stoichiometric amount of a mineral acid, such as HCl, HBr, H$_2$SO$_4$ or H$_3$PO$_4$ or of an organic acid such as acetic, propionic, valeric, oleic, palmitic, stearic, lauric, benzoic, lactic, paratoluenesulfonic, methane sulfonic, citric, maleic, fumaric, succinic and the like, respectively.

The compounds of formula I above may be prepared by the methods described below with reference to Schemes 1 and 2.

Formula Scheme 1

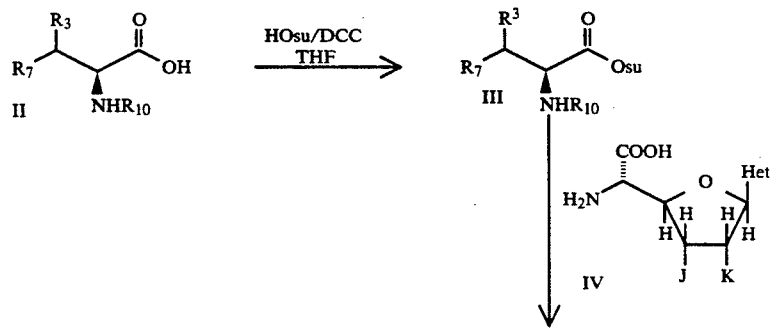

-continued

Formula Scheme 1

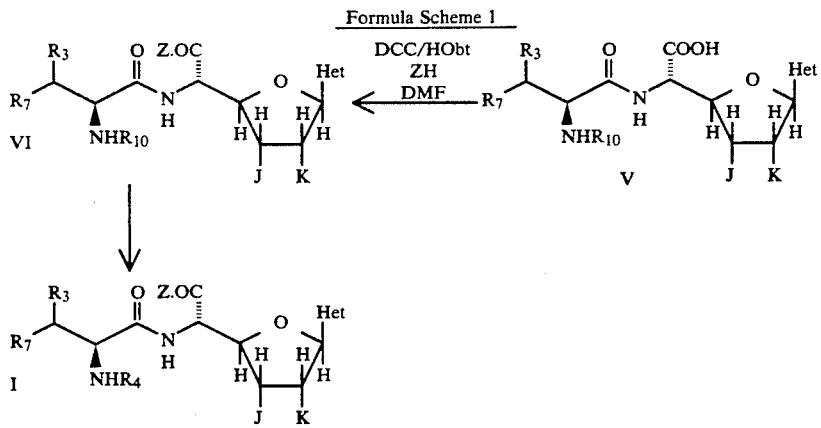

wherein $R_3$, $R_4$, $R_7$, Het, J, K, and Z are as described above unless otherwise indicated, and $R_{10}$ is an N-blocked natural amino acid, or an N-blocked metabolizable group; or a nitrogen protecting group such as tert-butoxycarbonyl or benzyloxycarbonyl.

As used herein Osu denotes N-oxysuccinimide, HOsu denotes N-hydroxysuccinimide, DCC denotes 1,3-dicyclohexylcarbodiimide, HObt denotes N-hydroxybenztriazole, DMF denotes N,N-dimethylformamide, (BOC)$_2$O denotes ditert.butyldicarbonate.

The compounds of formulas II and IV are known, can be prepared in accordance with known methods, or else their preparation is described herein.

A compound of formula II may converted to the corresponding N-oxysuccinimide ester of formula III by reaction with N-hydroxysuccinimide in an aprotic, organic solvent such as N,N-dimethylformamide, acetonitrile, ethyl acetate, methylene chloride, or more preferably, tetrahydrofuran in the presence of a carbodiimide such as 1,3-dicyclocarbodiimide, and at a temperature in the range of about 0° to about 40° C. or more preferably 20° C. The resulting active ester of formula III may be isolated by conventional means such as crystallization or chromatography, or it may be used directly in the next step of a synthesis of this invention.

PROCEDURE A

The N-oxysuccinimide ester of formula III may be reacted with a uracil polyoxin C compound of formula IV

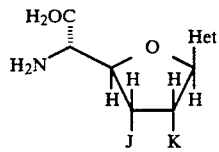

wherein J, K, and Het are as described above, to obtain a compound of formula V. The reaction is run in a polar, aprotic, organic solvent such as N,N-dimethylformamide, acetonitrile, tetrahydrofuran, or more preferably, dimethylsulfoxide. The reaction is run under an inert atmosphere such as argon or nitrogen. The reaction is run at a temperature in the range of about to 20° C. to about 50° C., more preferably, at room temperature. The resulting compound of formula V may be separated by conventional means such as crystallization or chromatography, or it may be used directly in the next step of a synthesis of this invention.

PROCEDURE B

A compound of formula V may be reacted with an amine $R_5NR_6$ (wherein $R_5$ and $R_6$ are as described herein) to obtain a compound of formula VI. The reaction is run in a polar, aprotic, organic solvent such as acetonitrile, tetrahydrofuran, or more preferably, dimethylformamide, in the presence of a carbodiimide, such as dicyclohexylcarbodiimide, and in the further presence of an activating reagent such as N-hydroxysuccinimide, or more preferably 1-hydroxybenztriazole. The reaction is run at a temperature in the range of about 0° to about 50° C., more preferably, room temperature. The resulting compound of formula VI may be separated by conventional means such as crystallization or chromatography, or it may be used directly in the next step of the synthesis of this invention.

The next step of the synthesis is the deprotection of the —$NHR_{10}$ group of a compound of formula VI to obtain a compound of formula I.

In the case of the tert-butoxycarbonyl (BOC) protecting group, a compound of formula VI may be converted to a final product of formula I of the invention by treatment with a mineral acid such as hydrochloric acid or sulfuric acid, or more preferably, the organic acid trifluoroacetic acid at a temperature in the range of about 0° C. to about 25° C., more preferably, room temperature. A compound formula I of the invention may be separated from the reaction mixture by conventional means such as crystallization or chromatography.

In the case of the benzyloxycarbonyl (CBZ) protecting group, a compound of formula VI may be hydrogenolized by dissolving it in a solvent such as ethanol, or more preferably, 95% methanol and 5% formic acid in the presence of a catalyst which facilitates hydrogenolysis such as palladium on carbon, or more preferably palladium black. After deprotection is complete, the palladium may be filtered and the filtrate evaporated under reduced pressure at 50° C. to obtain a compound of formula I of the invention. This compound of formula I may be further purified by conventional means such as crystallization or chromatography.

Alternatively, the compounds of formula I of the invention may be prepared in accordance with Formula Scheme 2 below Formula Scheme 2

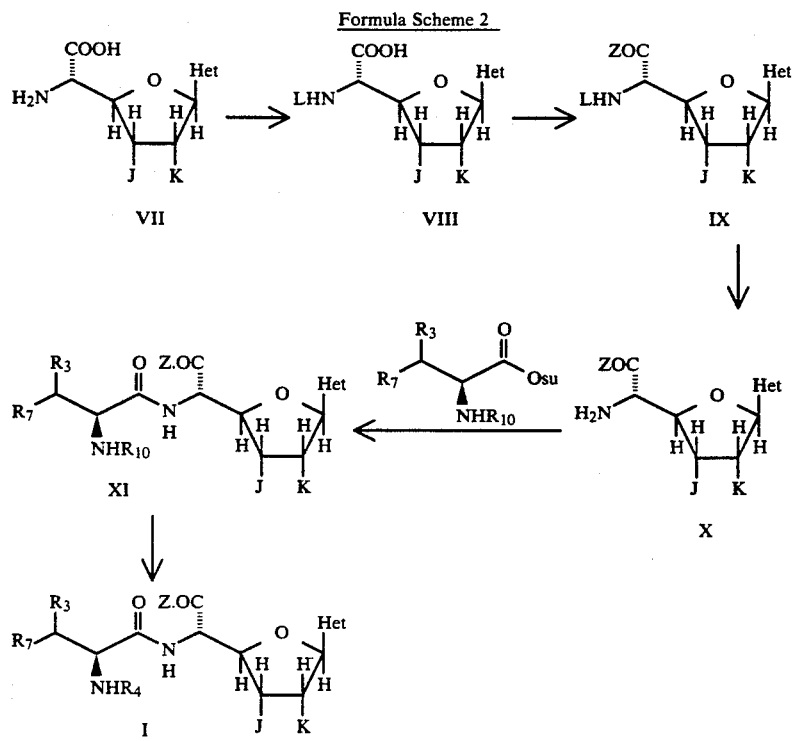

wherein $R_3$, $R_4$, $R_5$, $R_6$, $R_7$, $R_{10}$, J, K, Z, and Het are as described herein and L is a nitrogen protecting group such as tert-butoxycarbonyl or benzyloxycarbonyl.

PROCEDURE C

A compound of formula VII may be reacted with di-tert. butyldicarbonate to obtain a compound of formula VIII. The solvent employed is a polar solvent such as methanol, N,N-dimethylformamide, or more preferably, water. The reaction is run at a pH in the range of about 8 to about 10, more preferably, 9.5. The reaction mixture is kept basic through use of an alkali metal carbonate such as sodium carbonate or potassium carbonate, or through use of an alkali metal hydroxide such as potassium hydroxide or, more preferably, sodium hydroxide. The reaction is run at a temperature in the range of about 0° to about 25° C., more preferably about room temperature.

The resulting compound of formula VIII may be separated by conventional means such as crystallization or chromatography, or it may be used directly in the next step of the synthesis of this invention.

A compound of formula VIII may be reacted with an amine $R_5NR_6$ (wherein $R_5$ and $R_6$ are as described herein) to obtain a compound of formula IX. The reaction is run in a polar organic solvent such as acetonitrile, tetrahydrofuran, or more preferably, dimethylformamide, in the presence of a carbodiimide, such as dicyclohexylcarbodiimide, and in the further presence of an activating reagent such as N-hydroxysuccinimide, or more preferably 1-hydroxybenztriazole. The reaction is run at a temperature in the range of about 0° to about 50° C., more preferably, room temperature. The resulting compound of formula IX may be separated by conventional means such as crystallization or chromatography, or it may be used directly in the next step of the synthesis of this invention.

Amines of formula $R_5NR_6$ are known or may be prepared in accordance with known methods

PROCEDURE D

A compound of formula IX may be converted to a compound of formula X by reaction in a mineral acid such as hydrochloric acid or sulfuric acid, or more preferably, the organic acid trifluoroacetic acid. The reaction is run at a temperature in the range of about 0° to about 25° C., more preferably room temperature. The resulting compound of formula X may be separated by conventional means such as crystallization or chromatography, or it may be used directly in the next step of the synthesis of this invention.

A compound of formula X may be converted to a compound of formula XI by reaction with an N-oxysuccinimide ester of a N-blocked-amino acid of the formula

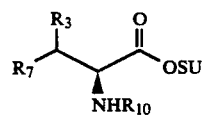

wherein $R_3$, $R_7$, $R_{10}$, are as described herein, in an anhydrous polar organic solvent such as methyl sulfoxide, tetrahydrofuran, acetonitrile, or more preferably dimethylformamide, in the presence of a tertiary amine base such as diisopropylethylamine, N-methyl morpholine, or more preferably triethylamine, at a temperature in the range of about 0° to about 50° C., or more preferably room temperature. The resulting compound of formula XII may be separated by conventional means such as crystallization or chromatography, or it may be used directly in the next step of the synthesis of this invention.

The next step of the synthesis is the deprotection of —NHR$_{10}$ group of a compound of formula XI to obtain a compound of formula I.

In the case of the tert-butoxycarbonyl (BOC) protecting group, a compound of formula XI may be converted to a final product of formula I of the invention by treatment with a mineral acid such as hydrochloric acid or sulfuric acid, or more preferably, the organic acid trifluoroacetic acid, at a temperature in the range of about 0° to about 25° C., more preferably room temperature. A compound formula I of the invention may be separated from the reaction mixture by conventional means such as crystallization or chromatography.

In the case of the benzyloxycarbonyl (CBZ) protecting group, a compound of formula XI may be hydrogenolized by dissolving it in a ethanol, or more preferably, 95% methanol and 5% formic acid in the presence of a catalyst which facilitates hydrogenolisis such as palladium on carbon, or more preferably, palladium black. After deprotection is complete, the palladium may be filtered and the filtrate evaporated under reduced pressure at 50° C. to obtain a compound of formula I of the invention. This compound of formula I may be further purified by conventional means such as crystallization or chromatography.

Compounds of formula VII are known, may be prepared in accordance with known methods, or else they may be prepared as described herein.

Compounds of the formula

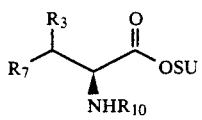

are known, may be prepared in accordance with known methods, or else they may be prepared as described herein.

RESULTS

The minimum inhibitory concentrations (MIC-R and MIC-S) for a series of compounds of formula I of the invention are as shown in Table 1 below.

The minimum inhibitory concentrations (MIC-R and MIC-S) were determined in accordance with the procedure set forth just below.

In vitro anti-fungal activity was determined in microtiter minimum inhibitory concentration (MIC) tests using Yeast Nitrogen Broth (YNB without amino acids, Difco., Detroit, Mich.) at pH 5.4. Yeasts were grown overnight in Sabouraud Dextrose Broth. at 28° C. with shaking, and concentrations adjusted in sterile saline using a spectrophoptometer at 540 mµ. Compounds were dissolved in various vehicles and diluted in media to twice the final concentrations. The Cetus Pro/Pette system was used to serially dilute 50 µl in round bottom 96 well plates (Falcon, Lincoln Park, NJ.). The turbidometrically adjusted yeast suspensions were diluted 1:3,000 in YNB. These dilutions when added to the wells, produced a final inoculum of $3 \times 10^3$/ml. Plates were incubated at 37° C. for 48 hours. MICs were defined as the lowest concentrations of compound that prevented visible growth. MICs were taken against the following organisms and expressed in the table above as the geometric mean. MIC-R and MIC-S mean respectively, MICs taken against resistant and sensitive strains.

| Resistant Strains |
| --- |
| Candida albicans C79 |
| Candida albicans C6 |
| Candida albicans C8 |
| Candida albicans C31 |
| Candida albicans C54 |
| Candida albicans C70 |
| Candida albicans C104 |
| Candida albicans C138 |
| Candida albicans C140 |
| Candida stellatoidea C45 |
| Sensitive Strains |
| Candida albicans C141 |
| Candida sp. C2 |
| Candida sp. C109 |
| Candida parapsilosis C67 |
| Candida tropicalis C112 |
| Torulopsis glabrata C95 |
| Candida pseudotropicalis C967 |
| Candida gullermondii C137 |
| Sacchararomyces C78 |
| Sacchararomyces mutant C147 |

Table 1 below also gives molecular ion masses (MS or Mass Spec.) for these compounds.

TABLE 1

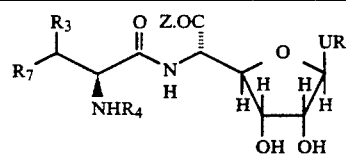

| No. | (structure) | Z.OC | MIC-R µg/ml | MIC-S µg/ml | Mass Spec. |
| --- | --- | --- | --- | --- | --- |
| 1. | CH$_3$ / NH$_2$ | CONH(CH$_2$)$_{11}$CH$_3$ | 18 | 26 | 565 |

TABLE 1-continued

[Structure: R7-CHR3-CH(NHR4)-C(=O)-NH-CH(Z.OC)-CH(OH)-CH(OH)-CH(H)-UR with O linkage]

[Partial structure shown: R7-CHR3-C(NHR4)-CO]

| No. | NHR4 structure | Z.OC | MIC-R µg/ml | MIC-S µg/ml | Mass Spec. |
|-----|----------------|------|-------------|-------------|------------|
| 2. | CH3-S(=O)-CH2CH2-CH(NH2)-CO | CONH(CH2)11CH3 | 181 | 181 | 601 |
| 3. | CH3-S-CH(CH3)-CH(NH2)-CO | CONH(CH2)11CH3 | 23 | 34 | 599 |
| 4. | H2N-C(=O)-O-CH2-CH(OH)-CH(OH)-CH(NH2)-CO | CONH(CH2)11CH3 | >478 | >416 | 644 |
| 5. | CH3-O-CH2CH2-CH(NH2)-CO | CONH(CH2)11CH3 | 52 | 111 | 569 |
| 6. | PhCH2-S-CH2-CH(NH2)-CO | CONH(CH2)11CH3 | 111 | >147 | 647 |
| 7. | CH3(CH2)9-CH(NH2)-CO | CONH2 | >256 | >256 | 483 |
| 8. | CH3-(CH2)3-CH(NH2)-CO | CONH(CH2)11CH3 | 13 | 19.7 | 567 |
| 9. | norbornyl-CH(NH2)-CO | CONH(CH2)11CH3 | 104 | 315 | 591 |

As can be seen from the above table, compounds of the invention exhibit anti-fungal activity against human and animal pathogens which are both sensitive to nikkomycins (MIC-S µg/ml < 128) and resistant to nikkomycins (MIC-R µg/ml > 2048).

In vivo anti-fungal activity was tested for in the following test protocol. Compounds of the invention were found to be active in the following test protocol.

MATERIALS AND METHODS

Vaginal Candida infections in hamsters

C. albicans (C60 or C79), clinical isolates, were grown on SDA slants for 48 hours at 28° C. Cells were washed off the slants with SDB broth to obtain a suspension of approximately $1 \times 10^8$ cells/ml. Groups of 10 female Syrian outbred hamsters (Charles River), weighing 100-120 grams, were used. On the first day of the experiment, the vagina was swabbed with a dry cotton swab to remove any mucus and to induce a slight irritation. The suspension of C. albicans (0.05 ml) was introduced into the vagina on three successive days using a syringe equipped with a blunt needle. Two days after infection, samples were obtained for culture by inserting a sterile cotton swab into the vagina. The swabs were placed into 10 ml of 0.9% saline containing cycloheximide (Actidione, Upjohn, 0.45 g/l) and chloramphenicol (Chloromycetin sodium succinate, Parke Davis, Morris Plains, N. J., 0.1 g/l), and then vigorously agitated to dislodge the vaginal sample. A 2 ml aliquot of each sample was then passed through a 0.45 micron Millipore filter. Following a saline rinse of the filters, the filters were placed onto mycosel agar plates and incubated at 37° C. After 48 h the number of C. albicans colonies on the filters were counted. Only animals that showed positive cultures were used for the experiments.

Treatment began 4 days after completion of infection. Compounds were solubilized in ethanol:PEG400: glycerol (10:45:45). Treatment was intravaginally at concentrations of 0.125-2% once daily for 4 days. Using cotton swabs, vaginal samples were obtained after 2, 4, 7 and 9 days of treatment and the swabs were processed as above. Efficacy was determined on the basis of negative cultures at each of the four time periods.

MATERIALS AND METHODS

C. albicans infection studies in mice ($PD_{50}$)

C. albicans Wisconsin (C 43) and C. tropicalis (C 112), grown on Sabouraud dextrose agar (SDA) slants for 48 h at 28° C., were suspended in saline and adjusted to 46% transmission at 550 nm on a spectrophotometer. The inoculum was further adjusted by hemacytometer and confirmed by plate counts to be approximately 1 or $5 \times 10^7$ CFU/ml. CF-1 mice (white, male, ca. 20 g, Harlan Sprague Dawley, Inc., Indianapolis, Ind.) were infected by injection 1 or $5 \times 10^6$ CFU into the tail vein. Antifungal agents were administered intravenously or subcutaneously in ethanol:water (10:90), 4 h post infection and once daily thereafter for 3 or 4 more days. Survival was monitored daily. The protective dose$_{50}$ ($PD_{50}$) was defined as that dose which allowed for 50% survival of mice.

The pharmaceutical compositions of the present invention may be formulated by combining a compound of the invention or pharmaceutically acceptable salt thereof with any suitable diluent, i.e., inert pharmaceutical carrier or diluent adapted for administration orally, parenterally, topically, vaginally or rectally.

Examples of suitable compositions include solid or liquid compositions for oral administration such as tablets, capsules, pills powders, granules, solutions, suspensions or emulsions. They may also be manufactured in the form of sterile, solid compositions which can be dissolved in sterile water, physiological saline or some sterile, injectable medium immediately before use.

Topical dosage forms may be prepared according to procedures well known in the art, and may contain a variety of ingredients, excipients, and additives. The formulations for topical use include ointments, creams, lotions, powders, aerosols, pessaries, and sprays. Of these, lotions, ointments, and creams, may contain water, oils fats, waxes, polyesters, alcohols or polyols, plus such other ingredients as fragrances, emulsifiers, and preservatives. Powders are made by mixing the active ingredient with a readily available, inert, pulverous distributing agent such as talcum, calcium carbonate, tricalcium phosphate, or boric acid. Aqueous suspensions of the above powders may also be made. Solutions or emulsions may also be prepared using inert solvents which are preferably nonflammable, odorless, colorless, and nontoxic, for example, vegetable oils, isopropanol, dimethyl sulfoxide, hydrogenated naphthalenes, and alkylated naphthalenes. Similarly, aerosol, and non aerosol sprays may be prepared using solutions or suspensions in appropriate solvents, for example, difluorodichloromethane for aerosols.

Parenteral forms to be injected intravenously, intramuscularly, or subcutaneously, are usually in the form of a sterile solution, and may contain salts or glucose to make the solution isotonic.

Compounds of the invention may also be incorporated in vaginal or rectal suppositories. Suppositories may be prepared by methods which are conventional in the art. In addition to comprising a compound of the invention, suppositories may contain a suppository base made up of biocompatible polymers, a surfactant, and an absorbent in a vegetable oil phase.

In addition, the suppositories may be further modified by inclusion of an antioxidant.

When used orally or parenterally, the compounds of the invention can be administered in an amount ranging from about 0.02 mg/kg body weight to about 40.0 mg/kg body weight, preferably from about 0.1 mg/kg body weight to about 20 mg/kg body weight per day.

Determination of the proper dosage of a compound of the invention for a particular situation is within the skill of the art. Generally, treatment is initiated with smaller dosages that are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of formula I and the pharmaceutically acceptable salts thereof will be regulated according to the judgment of the attending clinician considering such factors as age, condition, size of the patient, severity of the symptom being treated, and the pharmacokinetics of the particular compound being employed.

The invention disclosed herein is exemplified by the following preparative examples, which should not be construed to limit the scope of the disclosure. Alternative mechanistic pathways and analogous structures within the scope of the invention may be apparent to those skilled in the art.

EXAMPLE 1

Preparation of N-BOC-UPOC

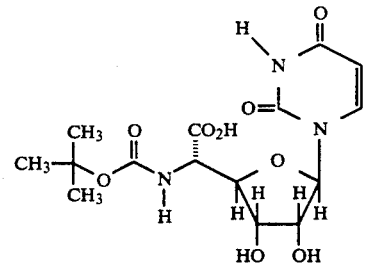

UPOC (8 g, 27.8 mmol) was dissolved in 200 ml of distilled water. The solution was stirred and the pH was adjusted to 9.5 with 20% sodium hydroxide solution. At room temperature di-tert. butyldicarbonate (8 g, 36.7 mmol) was added all at once and stirred while the pH was monitored at 9.5 with sodium hydroxide. After approximately 5 hours or after the reaction was complete by thin layer chromatography (tlc) (40% methanol-methylene chloride, normal phase silica plates) Dowex XFS-43279.00 hydrogen from resin was added to pH 3.0. The resin filtered off and the solvents were evaporated off under reduced vacuum at 45° C. The resulting solid was dissolved in 100 mL of methanol and added to stirring ether. The precipitate was filtered off and dried in a vacuum desiccator to obtain 10.5 g (97%) of the title product.

$^1$H-NMR (300 MHZ, CD$_3$OD) δ 7.70 (1H, d, J=7.5 Hz), δ 5.92 (1H, d, J=6 Hz), δ 5.70 (1H, d, J=7.5 Hz),

δ 4.39 (1H, m,), δ 4.32 (1H, m), δ 4.23 (1H, m), δ 4.12 (1H, t, J=5.25 Hz), δ 1.45 (1H,s).

EXAMPLE 2

Preparation of N-BOC-6'-dodecylamido-UPOC.

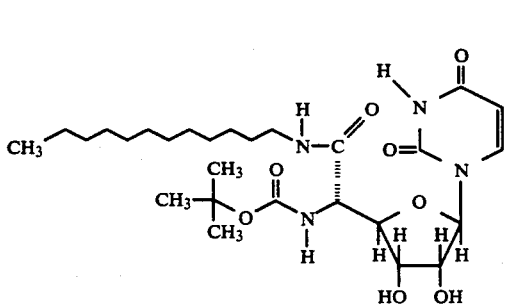

N-BOC-UPOC (5.2 g, 13.42 mmol) was dissolved in 150 ml of dry N,N-dimethylformamide (DMF). Dodecylamine (3.73 g, 20.13 mmol), dicyclohexylcarbodiimide (5.538 g, 26.84 mmol), and 1-hydroxybenztriazole (2.26 g, 16.77 mmol) were added and the resulting mixture was stirred at room temperature. After 48 hours, 2 ml of H₂O were added and the resulting mixture was stirred for 15 minutes. The precipitate was filtered off and the solvent, DMF, was evaporated under high vacuum at 50° C. to obtain an oil. The oil was chromatographed on silica gel using 1.25% to 5% methanol-methylene chloride to obtain 6.3 g (84%) of the title product.

EXAMPLE 3

6'-Dodecylamido-UPOC-trifluoroacetate

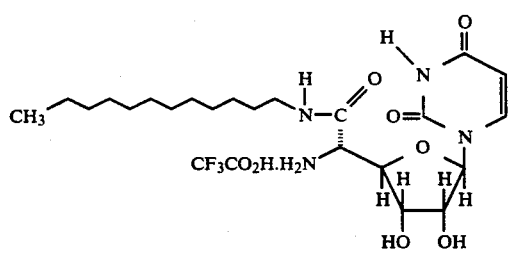

N-BOC-6'-dodecylamido-UPOC (6.25 g, 11.25 mmol) were dissolved in 15 ml of trifluoroacetic acid and the resulting mixture was stirred at room temperature for 5 minutes. 100 ml of ether were added and the solids were filtered off to obtain 6.01 g of title product after drying in a vacuum desiccator.

¹H-NMR (300 MHZ, D₂O) δ7.62 (1H, d, J=8.07 Hz), 5.66 (1H, d, J=8.01 Hz), 5.49 (1H, d, J=8.87 Hz) 4.28 to 4.34 (2H, m), 4.16 (1H, t, J=4.95 Hz), 4.08 (1H, d, J=5.22 Hz), 1.46 (2H, m), 1.22 (20H, br.s), 0.835 (3H, t, J=6.99 Hz).

EXAMPLE 4

Preparation of 6'-dodecylamido-5-N-[2-S-(t-butyloxycarbonyl)amino-3-methyl-4-pentenoyl]-UPOC

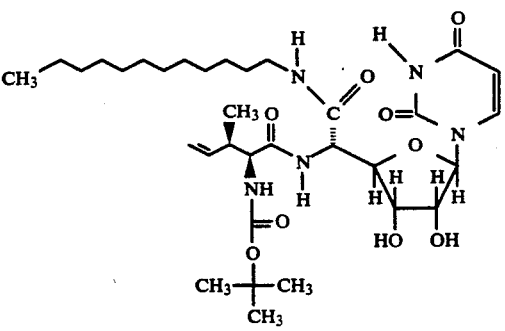

2-S-(t-butyloxycarbonyl)amino-3-R-methyl-4-pentenoic acid (0.575 g, 2.5 mmol) was dissolved in DMF (15 ml), and N-hydroxysuccinimide (0.35 g, 3 mmol) was added. The solution was cooled to 0°-5° C., DCC (0.555 g, 2.7 mmol) was added and the resulting solution was stirred at 0°-5° C. for ½ hour, then 18 hours at room temperature. The mixture was filtered to remove the precipitated urea, and the filtrate was added to a solution of N-BOC-6'-dodecylamido-UPOC (1.4 mmol), DMF (6 ml), and Et₃N (200 ml, 1.4 mmol). The resulting mixture was stirred for 48 hours, then concentrated to 10 ml and poured into cold water (200 ml). The mixture was filtered to obtain the precipitate, and the precipitate was chromatographed on C-18 reverse-phase silica gel (4:1 MeOH-H₂O, 0.1% TFA) to obtain 0.62 g (57%) of title compound, which was deprotected without further purification.

EXAMPLE 5

Preparation of 6'-dodecylamido-5-N-[2-S-amino-3-R-methyl-4-pentenoyl]-UPOC

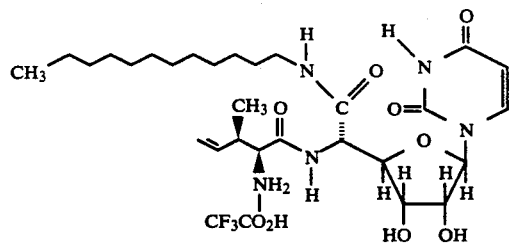

To 6'-dodecylamido-5-N-[2-S-(t-butyloxycarbonyl)amino-3-R-methyl-4-pentenoyl]-UPOC (0.62 g, 1 mmol) was added an ice-cold solution of 95:5 (v/v) TFA-MeOH (15 ml) and the resulting mixture was stirred at 0°-5° C. for 20 minutes. The solution was poured into cold water (400 ml), stirred for 5 minutes. The precipitate of crude product was filtered, washed, and dried This solid was then triturated with Et₂O in a sonication bath, and filtered to leave 0.63 g (93%) of monohydrate trifluoroacetate of the title product.

TFA means trifluoroacetic acid.

FABMS is 566 (100%, M⁺+1).

19

EXAMPLE 6

Preparation of
2-S-N-BOC-amino-3-R-methyl-pentenoic acid

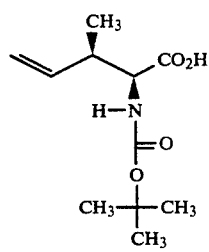

For the preparation of the racemic mixture of the formula just above, see P. A. Bartlett and J. F. Barstow, J. Org. Chem. 47, 3933-3941 (1982). 2-R,S-N-BOC-amino-3-R,S-methyl-pentenoic acid was resolved into its 2-S configuration as follows: To stirring trifluoroacetic acid (75 ml) was added 2-R,S-N-BOC-amino-3-R,S-methyl-pentenoic acid (25.79 g) portionwise. The mixture was stirred until dissolved. 200 ml of diethyl ether was slowly added to obtain 21.63 g after drying. The solid was dissolved in 250 ml of distilled water and cooled in an ice bath. The pH was adjusted to 9-9.5 with 25% NaOH. Acetic anhydride (25 ml) was dripped in while maintaining the pH at 9-9.5 with 25% NaOH. After thin layer chromatography (tlc) indicated completion of reaction, concentrated hydrochloric acid was added until the pH=2.0. The mixture was extracted with 4×200 ml of ethyl acetate, dried over magnesium sulfate, filtered, and evaporated to obtain 14.8 g of an oil. The oil of 2-R,S-N-acetyl-3-R,S-methyl-pentenoic acid was dissolved in 1 L of water. The pH was adjusted to 7.9 with 2N LiOH. Acylase I was added and the mixture was stirred for 1 hour. The mixture was then allowed to stand at 37° C. for 72 hours. The pH was adjusted to 4.9 with acetic acid, charcoal was added, and the resulting mixture was stirred for 1 hour. The mixture was filtered on a celite pad, added to a 500 ml column of XFS-43279.00 resin in the hydrogen form, and washed with 2 l of distilled water. The compound was eluted with ammonium hydroxide (50 ml of 30% diluted to 1 l of water). The column was monitored by tlc. The eluent containing the product was concentrated to obtain 4.97 g of title product after drying. $H^1$-NMR, M.S., and CHN identical to the unresolved product reported in the Bartlett paper. Preparation of 2-S-N-BOC-allo-isoleucine in the example just below confirmed the S conformation of the title product of the present example.

EXAMPLE 7

Preparation of
Methyl-2-S-N-fluorenylphenylamino-3-R,S-methyl-4-bromo-butyrate

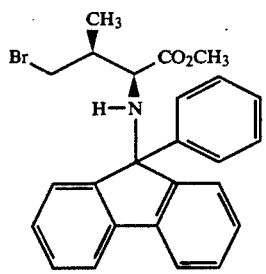

1 g of methyl-2-S-N-fluorenylphenyl-3-methyl-4-hydroxy butyrate (preparation as described in H. Rapoport and J. Wolf, J. Org. Chem. 54, 3164 (1989)) was dissolved in tetrahydrofuran. Carbon tetrabromide (1.57 g) and triphenylphosphine (1.26 g) was added and the mixture was stirred at room temperature for 4 hours. The mixture was added to brine and extracted with ethylacetate. The ethyl acetate layer was dried over magnesium sulfate, filtered, and evaporated to dryness. The mixture was chromatographed on a silica gel column using a mixture of 5% ethyl acetate/hexanes as the eluent to obtain 1.07 g of the title product.

$^1$H-NMR (300 MHZ, CD$_3$OD) δ 1.06 (3H, d, J=6.8 Hz), 1.84-1.90 (1H, m), 3.21 (2H, d, J=6.8 Hz), 3.28 (3H, s), 7.162-7.47 (13H,m). FABMS 450 (M+1).

EXAMPLE 8

Preparation of
2-S-N-fluorenylphenylamino-3-R,S-methyl-4-thiomethyl-butyric acid

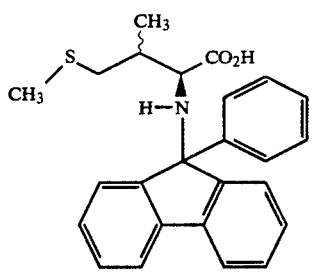

The preparation of this compound was identical to the preparation of 2-S-N-fluorenylphenyl-3-R,S-methyl-4-(1H-1,2,4-triazolyl)butyric acid except sodium thiomethoxide was used instead of sodium triazole to obtain the title product as a mixture of two compounds in the ratio of 2/1 in 40% yield.

The following table illustrates how other compounds of formula I of the invention may be made by using procedures analogous to those set forth above.

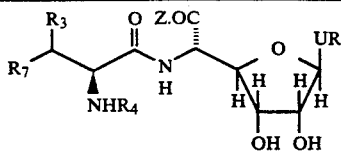

| No. | R₇ R₃ ⟨NHR₄ | Z.OC | Starting material | Process |
|---|---|---|---|---|
| 1. | CH₃ / CH=CH-CH-CH(NH₂)-CO | CONH(CH$_2$)$_{11}$CH$_3$ | Use 2-N-BOC-amino-3-methy-C-allyl glycine in procedure D | C/D |
| 2. | CH$_3$-S(=O)-CH$_2$CH$_2$-CH(NH$_2$)-CO | CONH(CH$_2$)$_{11}$CH$_3$ | Use L-Boc-methionine sulfoxide in procedure D | C/D |
| 3. | CH$_3$-S-CH(CH$_3$)-CH(NH$_2$)-CO | CONH(CH$_2$)$_{11}$CH$_3$ | Use N-fluorenylpyhenyl-L-3-methyl-methionine in procedure D | C/D |
| 4. | H$_2$N-COOCH$_2$-CH(OH)-CH(OH)-CH(NH$_2$)-CO | CONH(CH$_2$)$_{11}$CH$_3$ | Use N-BOC-polyoxin D instead of N-BOC UPOC in Procedure C | C/D |
| 5. | CH$_3$-O-CH$_2$CH$_2$-CH(NH$_2$)-CO | CONH(CH$_2$)$_{11}$CH$_3$ | Use N-BOC-L-methylhomoserine in procedure D | C/D |
| 5. | CH$_3$-O-CH$_2$CH$_2$-CH(NH$_2$)-CO | CONH(CH$_2$)$_{11}$CH$_3$ | Use N-BOC-L-methylhomoserine in procedure D | C/D |
| 6. | PhCH$_2$-S-CH$_2$-CH(NH$_2$)-CO | CONH(CH$_2$)$_{11}$CH$_3$ | Use N-BOC-L-3-thiobenzylalanine in procedure D | C/D |
| 7. | CH$_3$(CH$_2$)$_9$-CH(NH$_2$)-CO | CONH$_2$ | Use 2-amino-lauric acid for procedure A. Use ammonia in procedure B | A/B |
| 8. | CH$_3$-CH$_2$CH$_2$CH$_2$-CH(NH$_2$)-CO | CONH(CH$_2$)$_{11}$CH$_3$ | Use N-BOC-L-norleucine in procedure D | C/D |
| 9. | norbornyl-CH(NH$_2$)-CO | CONH(CH$_2$)$_{11}$CH$_3$ | Use 2-N-BOC-L-amino-2-norbornyl-carboxylic acid in procedure D | C/D69 |

What is claimed is:
1. A compound of the formula

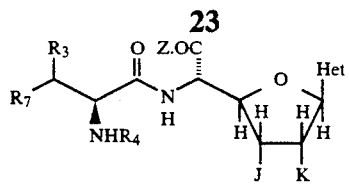

or a pharmaceutically acceptable salt thereof wherein;
Het is uracil
R₃ is H, OH, OCH₃, C₁-C₄alkyl, CF₃, or F
R₄ is H, a natural amino acid attached by a peptide bond, or a metabolizable group;
R₇ is

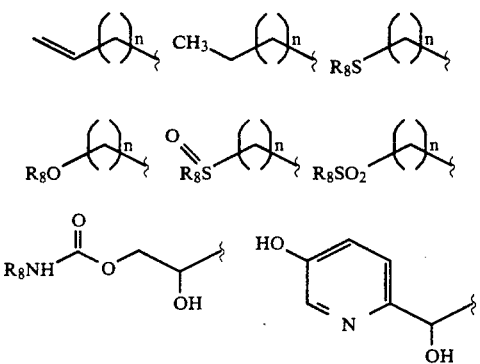

n is 1 to 16;
wherein Z is $R_5NR_6$.

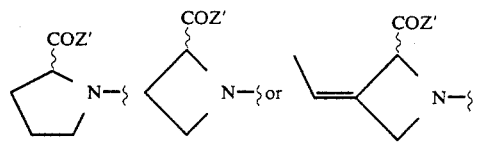

wherein Z' is $R_5NR_6$.
R₅ is —(CH₂)₁₁CH₃
R₆ is H; OH; O-benzyl; O-aryl; O-C₄-C₁₄alkyl; C₁-C₁₂alkyl; phenyl; substituted phenyl; or NHCO-R⁸;
R₈ is C₁-C₁₆alkyl; H, aryl or alkylaryl; with the proviso that R₈ cannot be H when when R₇ is

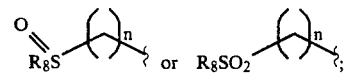

J is H, or OH; and
K is H, or OH.

2. A compound according to claim 1, wherein J and K are both OH.

3. The compound according to, claim 2 having the formula

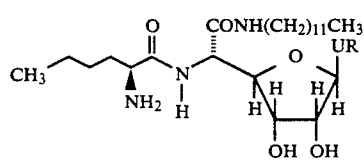

or a pharmaceutically acceptable salt thereof.

4. The compound according to claim 2,

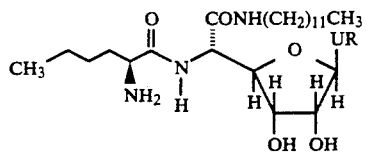

or a pharmaceutically acceptable salt thereof.

5. A compound according to claim 1 selected from the group consisting of

| No. | $R_7$—$\overset{R_3}{\underset{NHR_4}{C}}$—CO | Z.OC |
|---|---|---|
| 2. | CH₃—S(=O)—CH₂CH₂—CH(NH₂)—CO | CONH(CH₂)₁₁CH₃ |
| 3. | CH₃—S—CH(CH₃)—CH(NH₂)—CO | CONH(CH₂)₁₁CH₃ |
| 4. | H₂N—C(=O)—O—CH₂—CH(OH)—CH(OH)—CH(NH₂)—CO | CONH(CH₂)₁₁CH₃ |
| 5. | CH₃—O—CH₂CH₂—CH(NH₂)—CO | CONH(CH₂)₁₁CH₃ |
| 6. | PhCH₂—S—CH₂—CH(NH₂)—CO | CONH(CH₂)₁₁CH₃ |
| 8. | CH₃—(CH₂)₃—CH(NH₂)—CO | CONH(CH₂)₁₁CH₃ |
| 9. | norbornyl-CH(NH₂)—CO | CONH(CH₂)₁₁CH₃ | or a pharmaceutically acceptable salt thereof.

6. The compound of the formula

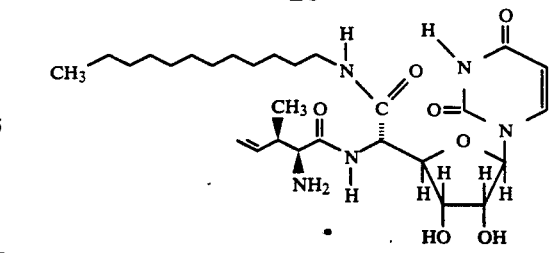

or a pharmaceutically acceptable salt thereof.

7. A pharmaceutical composition comprising an antifungally effective amount of a compound as defined in claim 1 in combination with a pharmaceutically acceptable carrier.

8. A method for treating a fungal infection in a mammal which comprises administering to the mammal an anti-fungally effective amount of a compound according to claim 1.

* * * * *